United States Patent [19]

Thompson

[11] 4,259,578
[45] Mar. 31, 1981

[54] MOVABLE COLLIMATOR FOR POSITRON ANNIHILATION IMAGING DEVICE

[76] Inventor: Christopher J. Thompson, 11870 Lavigne, Montreal, Quebec, Canada, H4J 1X8

[21] Appl. No.: 70,068

[22] Filed: Aug. 27, 1979

[51] Int. Cl.³ .................. G01T 1/20; G01N 21/00
[52] U.S. Cl. .................. 250/363 S; 250/366; 250/445 T
[58] Field of Search ............ 250/361 R, 363 S, 367, 250/445 T, 505, 511, 512, 513, 366

[56] References Cited

U.S. PATENT DOCUMENTS

| | | | |
|---|---|---|---|
| 2,852,684 | 9/1958 | Payne, Jr. | 250/511 |
| 4,150,292 | 4/1979 | Ter-Pogossian | 250/363 S |
| 4,176,280 | 11/1979 | Greschat et al. | 250/445 T |

Primary Examiner—Davis L. Willis
Assistant Examiner—Janice A. Howell
Attorney, Agent, or Firm—Beveridge, De Grandi, Kline & Lunsford

[57] ABSTRACT

A positron annihilation imaging device having two circular arrays of detectors disposed in spaced apart parallel planes wherein axially movable annular collimator rings are generally disposed in a pair of opposite planes outside the associated planes of the collimators to each collimator being movable toward the opposite collimator and a central collimator of annular configuration generally disposed between the two rows of detectors but being split into two rings which may be separated, the outer and inner collimators serving to enhance data readout and imaging.

7 Claims, 6 Drawing Figures

MOVABLE COLLIMATOR FOR POSITRON ANNIHILATION IMAGING DEVICE

BACKGROUND OF THE INVENTION

1. Field of the Invention

This invention relates generally to positron emission tomography and more particularly to devices which use an array of scintillation detectors to detect the annihilation radiation from positron disintegration and use this information to reconstruct an image of the distribution of positron emitting isotopes within a body.

2. Description of the Prior Art

Positron emission tomography is a technique for measuring the concentration of a positron emitting isotope through a sectional plane through the body. Normally the isotope is used to label a substance which circulates with the blood and may be absorbed in certain tissues. The technique allows the actual concentration in the slice to be determined if the device is suitably calibrated.

Certain isotopes decay by emitting a positively charged particle with the same mass as the electron (positron) and the neutrino from the nucleus. In this process one of the protons in the nucleus becomes a neutron, so that its atomic number goes down while its atomic weight remains constant. This positron is ejected with a kinetic energy of up to 2 MeV depending on the isotope and loses this energy and collisions while travelling a distance of up to a few mms in water. When it has reached thermal energies it interacts with an electron and they mutually anhilate one another. The rest mass of the 2 particles is transformed into 2 gamma rays of 511 keV which are emitted at 180° in the 'center of mass' coordinates of the original particles. The 2 gamma rays may be detected by suitable devices. If these devices measured the energy of the gamma rays at 511 keV and register this energy almost simultaneously it may be assumed that the original of the radiation is on a straight line between the 2 detectors. Several detectors may be used in an arrangement so that many coincident events may be imaged during the same time interval. Then the information from these detectors is processed by a computer using image reconstruction techniques in order to find the location of distribution of positron emitting isotope.

Components of imaging device

A device for imaging positron annihilation radiation consists of the following basic parts:

(1) A number of detectors arranged in a precise geometrical pattern. These detectors are normally scintillation detectors in one or several planes, and these detectors are normally arranged in a polygonal pattern or around the circumference of a circle. Scintillation detectors emit a light flash each time they absorb gamma radiation which may or may not arise from the mutual anhilation of a positron and electron. The intensity of the light flash is proportional to the gamma ray energy.

(2) The device must contain a means of converting the light flash to an electrical charge pulse, whose amplitude is proportional to the light intensity.

(3) The device must contain a means of determining that the charge pulse could have arisen from a gamma ray whose energy was approximately equivalent to the mass of the electron at rest (511 keV).

(4) The device must have an electric circuit capable of determining that 2 and only 2 detectors each recorded gamma rays of appropriate energy within a short time interval (coincidence resolving time). These detectors are said to have recorded a 'coincident event'.

(5) The device must have an electric circuit which determines which 2 detectors out of the many possible combinations recorded the so-called 'coincident event'.

(6) The device must have a memory in which it can record how often each pair of detectors record a 'coincident event'. The memory may be part of the random access memory of a general purpose computer.

(7) The device is required to use an algorithm through which the information in the memory may be transformed into an image of the distribution of positron anhilation per unit time in a cross-section surrounded by the detectors. The sequence of steps described by this algorithm may be programmed into a general purpose computer.

The main object of this invention is to provide a positron annihilation imaging device which has two or more rings of detectors from which 3 or more slices through the object being scanned can be determined at once, with a technique for adjusting the slice widths.

Another object of this invention is to allow one slice to be imaged by all detectors in adjacent planes simultaneously and reconstructed as if all detectors were in the same plane.

Another object of this invention is to provide the single slice facility without the necessity of rotating the detector array or moving it in any way during data collection. This allows for the possibility of doing physiologically gated imaging of a single slice without moving the detector array so that the rate of image collection is independent of detector movement and limited only by the permanent storage of data from individual images.

In accordance with the foregoing objects, there is provided:

A positron annihilation imaging device comprising:
(a) a first circular array of n detectors disposed in a first plane, said first detectors being equally spaced apart by an angle 360/n,
(b) a second circular array of detectors of the same number as for the first detectors disposed coaxially with said first row of detectors and in a second plane separated from said first plane, said second detectors being equally spaced apart by an angle 360°/n, the said second detectors being staggered from said first detectors by an angle substantially equal to 360°/2n,
(c) fixed first and second shield means disposed outside said rows of detectors, said shield means having flat annular configuration, said first and second arrays of detectors being circumferentially movable with respect to said fixed shield means by said angle 360/2n and,
(d) first and second outer collimator elements of flat annular configuration, said collimator elements being disposed between said fixed shield means and the associated circular array of detectors and in planes parallel therewith said first and second outer collimator elements being movable.

A preferred embodiment of the invention will now be described with reference to the accompanying drawings, in which.

DESCRIPTION OF A PREFERRED EMBODIMENT

Figure 1:
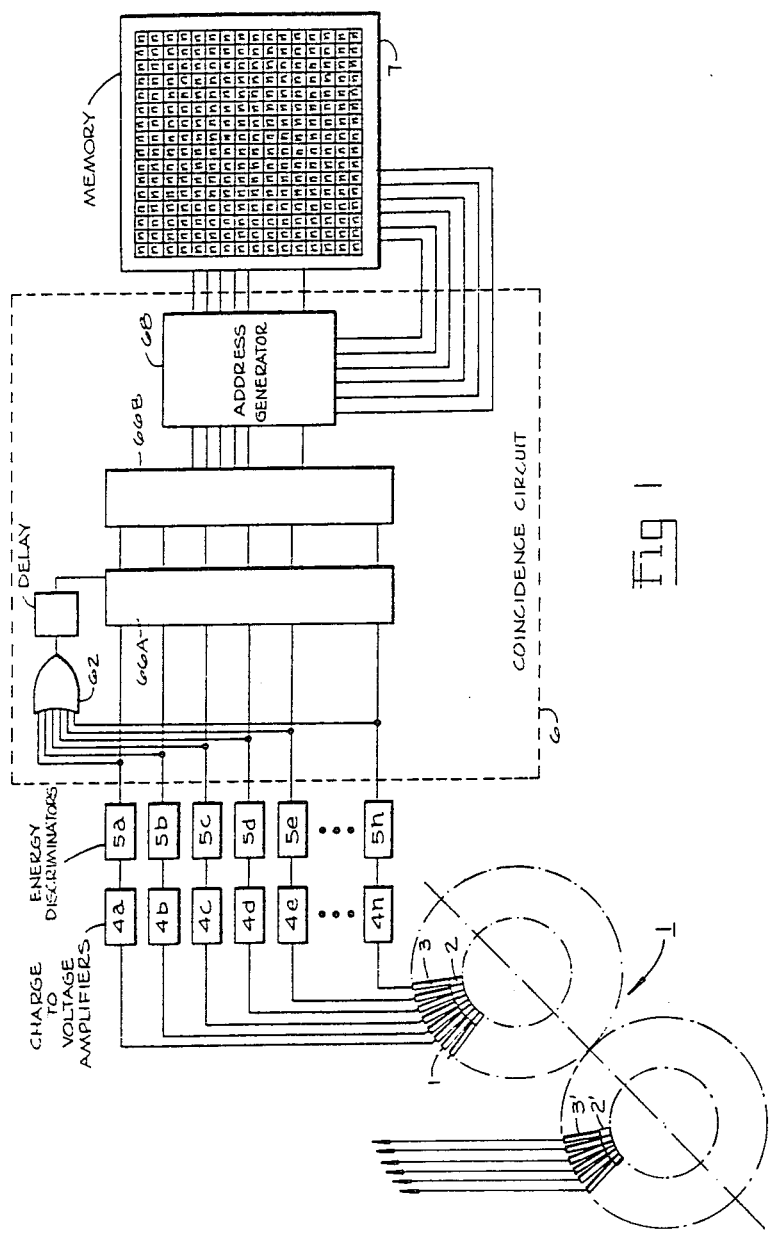
FIG. 1 is an overall block diagram of the apparatus.

The preferred embodiment of this positron anhilation imaging device 1 is shown in outline form in FIG. 1. It is seen that the device consists of two rings of detectors, 2 and 2', coaxially arranged, which surround the object being imaged in two planes. The signals from the detectors 2 and 2' are amplified in charge to voltage amplifiers 4 and their energy is measured by energy discriminators 5. The signals from the second ring of detectors 2' are similarly connected to change to voltage amplifiers 4 and energy discriminators 5. The outputs of each of the energy discriminators 5 are processed by a coincidence analysis circuit 6 which determines which two detectors were involved in any event. The output of the coincident circuit 6 is used to increment memory locations in a general purpose computer. The computer then reconstructs an image of the distribution emitting isotope in the cross-sections which were scanned. The aforementioned coincidence circuit is the subject of copending application Ser. No. 070,066 entitled "Coincidence Analysis Circuit for Positron Annihilation Imaging Device" filed Aug. 27, 1979 by Christopher John Thompson and assigned to the assignees of this application.

The preferred embodiment contains two rings of 64 trapezoidal shaped bismuth germanate detectors which are separated by thin tungsten septa. The shaped bismuth germanate detectors is the subject of copending application Ser. No. 70,372 filed Aug. 28, 1979 and assigned to the assignee of this application and entitled "Detector Shape and Arrangement for Positron Annihilation Imaging Device". These two rings of detectors are rotated with respect to one another by half the angular separation of the detectors (2.8°). This is the subject of co-pending application Ser. No. 70,067 filed Aug. 27, 1979 and assigned to the assignee of this application, and entitled "Positron Annihilation tion Imaging Device using Multiple Offset Rings of Detectors". FIG. 1 shows the two rings of detectors 2 and 2'.

Figure 2:
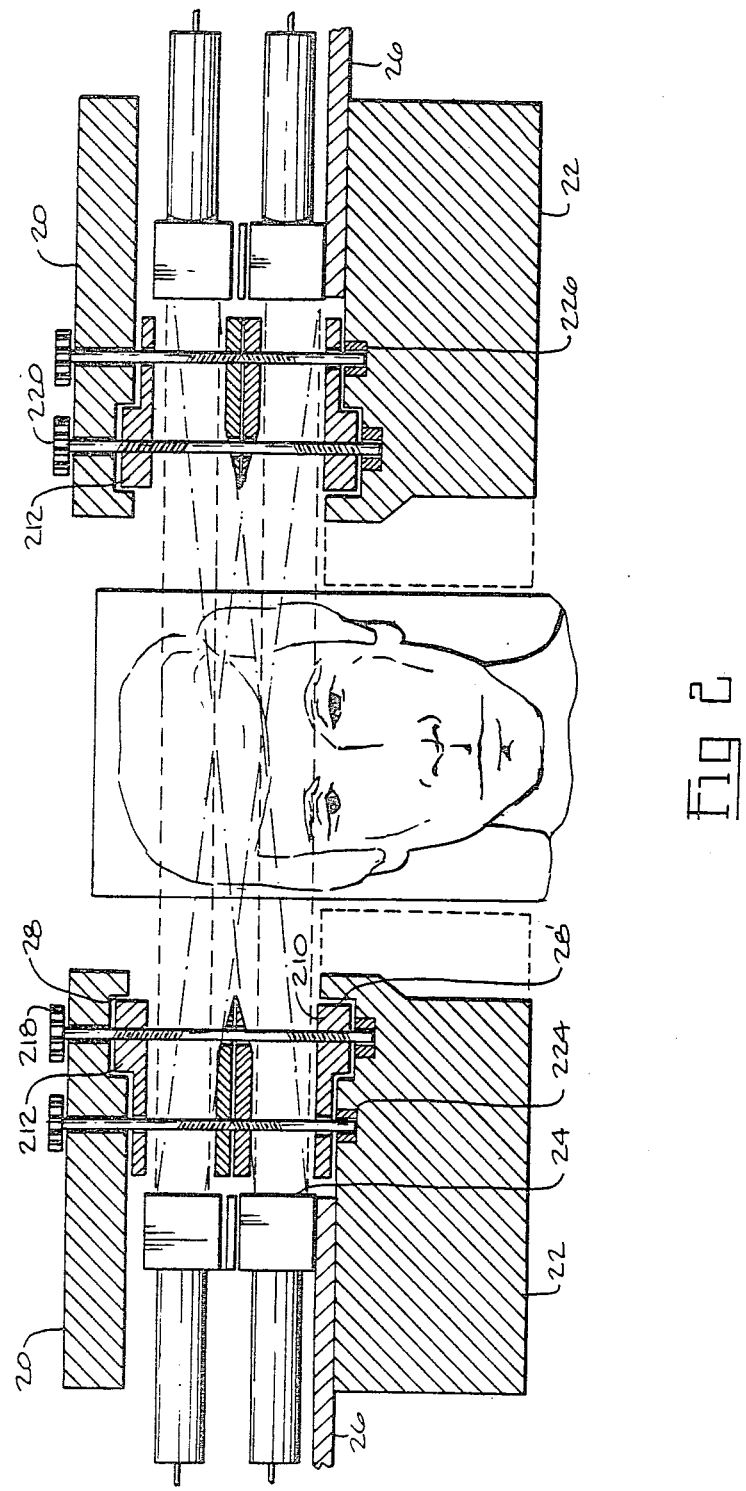
FIG. 2 is a plan view, partly in section, of the shielding and movable collimator assembly with the outer collimators retracted and the central collimator in its normal position allowing three images to be reconstructed.

Now referring to FIG. 2 in particular, it will be seen that the 2 rings of bismuth germanate detectors (c,d,e,f), carried by detector support plate 26, are surrounded by fixed lead shields 20 and 22. The purpose of these shields 20 and 22 is to prevent radiation, from outside the planes being imaged reaching the detectors and thus causing a random count background throughout the image. The inner face 24 of the detectors c,d,e and f, is on a circle 42 cm in diameter. The precise diameter is not critical. The detectors themselves are retained on the detector support plate 26 and are allowed to move with respect to the fixed lead shields 20 and 22. The detector array can rotate on its axis through an angle of 2.8° which, for the number of detectors used, is half the angular separation between two adjacent detectors. The simple to and fro rotary motion is used for low resolution studies. A high resolution mode can be obtained when the detector array, as a whole, is allowed to precess, about the coaxial axis, on a small circle (approximately 1 cm in diameter) which increases the number of samples per projection when the data is constructed.

Figure 6:
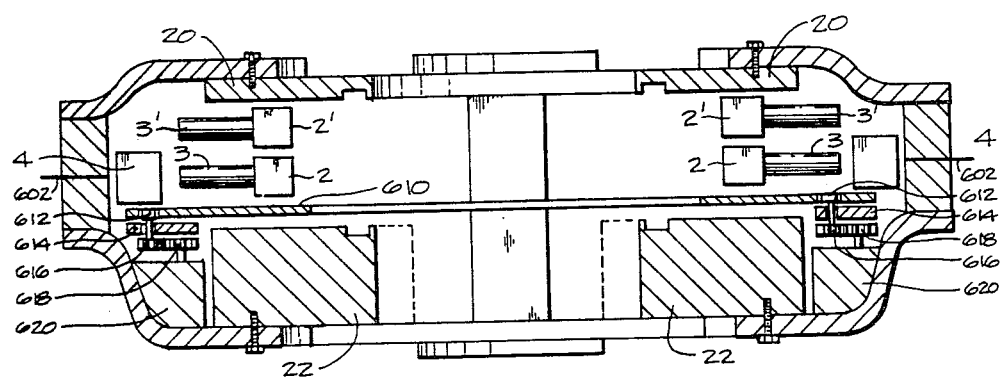
FIG. 6 is a cut away top view with the collimator removed showing the detectors, their support plate and the structure which holds the shielding.

The faces 24 of the fixed lead shields 20 and 24 which are closest to the detectors are circumferentially recessed at 28 and 28'. Within the recesses 28 and 28' on each of the lead shields 20 and 24, two movable lead collimator elements 210 and 212 can be placed. These two lead collimators which are annular in shape define the outer limits of the 2 outer slices and also the outer limits of the centre slice as shown in FIG. 2. The outer limits of the outer slices are shown in dashed lines between detectors C and D and detectors E and F. The outer limits of the centre slice is shown in solid lines which would occur for coincidences between detectors E and D and detectors C and F. The outer collimators can be moved in and out at will by means of the rotating screws 214 and 216 which are rotated by means of gears or sprockets 218, 220. There are eight such screws as shown in FIG. 6. The gears are connected by a drive belt 220 and a small reversible electric motor 224 rotates all of these screws synchronously moving the collimators in and out.

Figure 3:
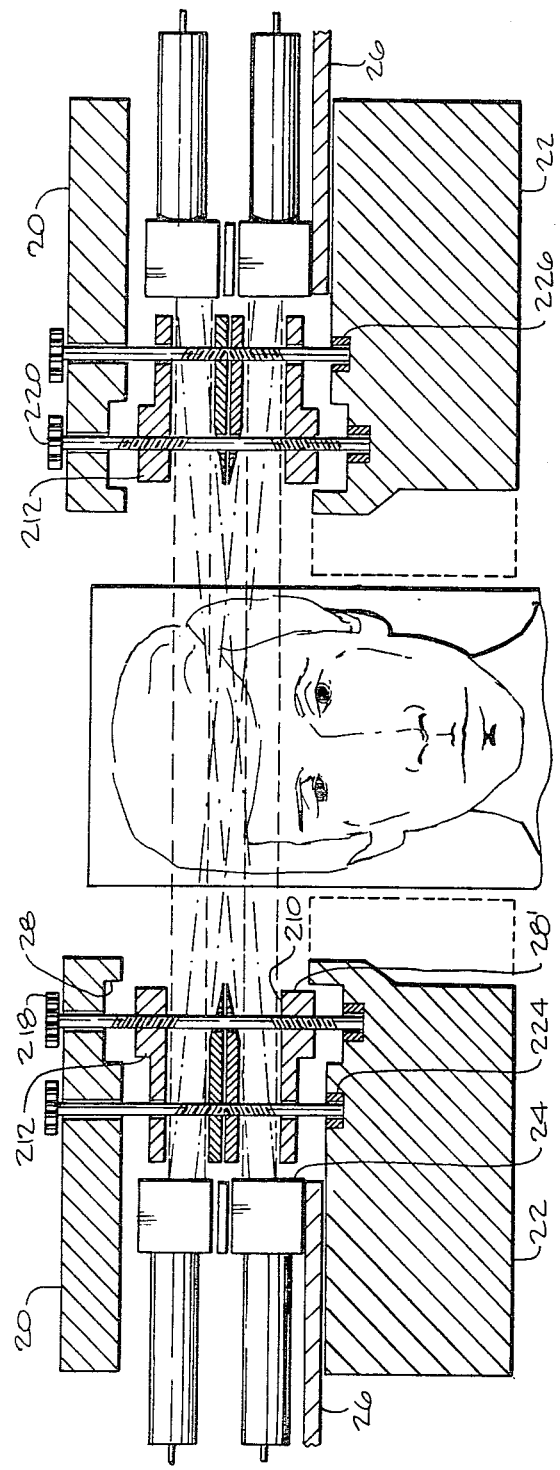
FIG. 3 is similar to FIG. 2 but with the outer collimators moved in towards the centre collimator to reduce the slice thickness of all slices simultaneously.

The upper and lower portions of the screws 214 and 216 have left and right-handed threads so that when the screws rotate in a clock-wise direction, the collimators move out from the central plane in unison. When the screws are rotated in a counter clock-wise direction, the 2 collimators move towards the central plane in unison. This movement can be appreciated by comparing FIGS. 2 and 3 in which the outer collimators 210 and 212 have been moved in towards the centre to a point where the slice width has been reduced to approximately 1.2 cm full width at half maximum (FWHM) from the normal thickness of 2 cm (FWHM).

Figure 4:
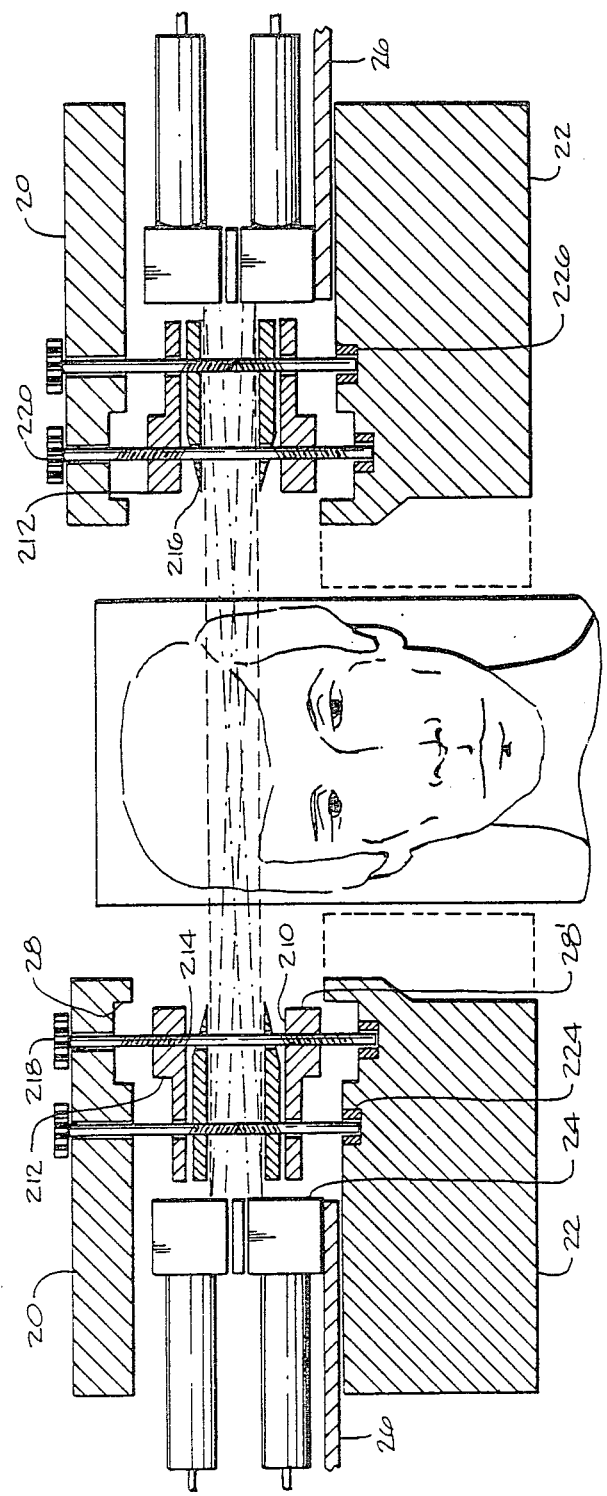
FIG. 4 is similar to FIG. 3 but now the centre collimator has been split and has been moved in parts out to the outer collimator allowing 1 slice to be reconstructed as if all 128 detectors were in the same plane.

In order to protect the detectors from radiation which comes from outside the plane, it is desirable to put central collimators 222/4 in between the two detectors. This is normally an annular piece of lead which is supported from the fixed lead shield 20. In this device however, the central collimater is made out of 2 tapered pieces of lead which can be moved on further lead screws 224 and 226 which have left and right-handed threads similar to that described for the outer collimator screws 214 and 216. The purpose of this is to allow the central collimator to be moved out of the way allowing a special imaging mode for 1 slice. This is shown clearly in FIG. 4 in which the half of the central collimator 222/4 and half 226 of the central collimator 216/218 have moved up against the outer slice collimator 212, and similarly for the lower halves of the central collimator.

Since the exposed faces of the detectors are now relatively small, a single image representing a slice approximately 2 cm across (FWHM) can be reconstructed from the data obtained from all 128 detectors simultaneously. Since the upper detector ring is rotated 2.8° with respect to the lower detector ring, the line joining detectors E and F is not directly above the line joining C and D but is, in fact, parallel to it and equally spaced between the line joining C and D and the lines joining the next two detectors in the lower ring. Thus the number of detector pairs available for image reconstruction is the same as if all 128 detectors were in the same ring. However, since the detectors are in fact much larger than one could obtain by putting 128 detectors in the same ring, this single slide mode is much more efficient than that which could be obtained by using 128 detectors of half the size of the detectors used in the preferred embodiment.

Furthermore, the width of the detectors is such that their aperture function is much wider than would be obtained with 128 detectors, thus providing a smoother sampling of the object to be scanned than would be obtained with 128 discrete detectors in a single plane.

Figure 5:
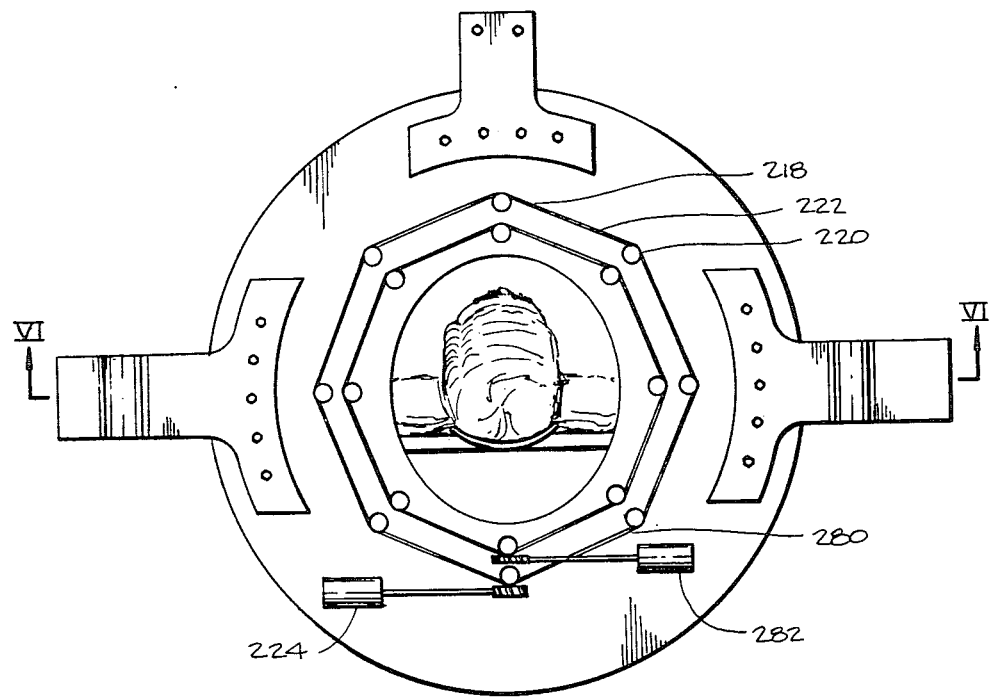
FIG. 5 is an elevation from the rear of the device showing the rear fixed shield and the sprocket drive and motors which move the collimators.

FIG. 5 shows the drive belt 280 and motor 282 assemblies for the lead screws which move the central collimator and the outer collimators. FIG. 5 also shows the way the lead shielding can be supported from a tilting bearing of the main detector assembly.

FIG. 6 shows a plan view of the whole detector and fixed shield assembly without the movable collimator. The detectors 2, 2' are attached to the detector support plate 610. The detector assembly can rotate and precess within the fixed shield assembly (20,20) the whole unit can tilt about the axis 602. The detector support plate rotates on a bearing 612, supported from the rotation support structure 614. This bearing is mounted eccentricly on the precession drive 616, 618. The precession drive is supported by the structure 620. Rotation of 618 causes the detector assembly to precess about a small circle.

Other embodiments falling within the terms of the appended claims will occur to those skilled in the art.

What is claimed is:

1. A positron annihilation imaging device comprising:
 (a) a first array of n detectors disposed in a first plane around an axis of symmetry, the detectors of said first array being equally spaced apart by a selected space;
 (b) a second array of detectors of the same number as for the first array of detectors, the detectors of said second array being disposed coaxially with said first array of detectors and in a second plane separated from said first plane, the detectors of said second array of detectors being equally spaced apart by the same selected space, the detectors of said second array of detectors being staggered from the detectors of said first array of detectors by a distance substantially equal to half the selected space;
 (c) fixed first and second shield means disposed outside said arrays of detectors, said shield means having a flat configuration;
 (d) first and second outer collimator elements of flat configuration, said collimator elements being disposed between said fixed shield means and the associated array of detectors and in planes parallel therewith said first and second outer collimator elements being selectively adjustable along said axis of symmetry; and
 (e) a central collimator of flat configuration disposed between said first and second planes.

2. Apparatus according to claim 1 wherein said central collimator is divided into two separate pieces, also of flat configuration, said separate pieces being axially movable along said axis of symmetry and separable into selected planes disposed between said fixed shield means and the associated first and second planes.

3. Apparatus according to claim 1, further including first actuator means for effecting simultaneous axial movement of said first and second collimator elements in opposite directions along said axis of symmetry, respectively.

4. Apparatus according to claim 3, wherein said first actuator means comprises a plurality of lead-screws having right and left-hand portions thereon.

5. Apparatus according to claim 2, further including second actuating means for separating said separable elements.

6. Apparatus according to claim 5 wherein said first actuator means comprises a plurality of lead-screws having right and left-hand portions thereof.

7. Apparatus according to claim 4 or 6 wherein said lead-screws are provided with sprockets, said sprockets being embraced by drive chains, said drive chains being adapted to be movable by reversible motor means.

* * * * *